United States Patent
Weichert et al.

(10) Patent No.: US 6,331,546 B1
(45) Date of Patent: Dec. 18, 2001

(54) USE OF 2-AMINO-3,4-DIHYDROQUINAZOLINES FOR THE PRODUCTION OF A MEDICAMENT FOR THE TREATMENT OR PROPHYLAXIS OF ILLNESSES CAUSED BY ISCHEMIC CONDITIONS

(75) Inventors: Andreas Weichert, Egelsbach; Udo Albus, Florstadt; Hans-Willi Jansen, Niedernhausen, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/696,233

(22) Filed: Oct. 26, 2000

(30) Foreign Application Priority Data

Oct. 27, 1999 (DE) ................................. 199 51 702

(51) Int. Cl.$^7$ ........................... A61K 31/505; A61P 9/10
(52) U.S. Cl. ............................................. 514/260
(58) Field of Search ............................................. 514/260

(56) References Cited

U.S. PATENT DOCUMENTS 3,560,601  2/1971  Walker .

FOREIGN PATENT DOCUMENTS 0 530 994  *  3/1993  (EP) .

530 994 A1  3/1993  (EP) .

OTHER PUBLICATIONS

Kosasayama et al., Cyclic Guanidines, Chem. Pharm Bull., 27(4), pp. 880–892 (1979).
Ishikawa et al., Cyclic Guanidines, Chem. Pharm Bull., 28(5), pp. 1357–1364 (1980).

* cited by examiner

Primary Examiner—Raymond Henley, III
(74) Attorney, Agent, or Firm—Finnegan, Henderson, Farabow, Garrett & Dunner, LLP

(57) ABSTRACT

Methods of using 2-amino-3,4-dihydroquinazolines of formula I, or a pharmaceutically tolerable salt thereof, for the treatment or prophylaxis of illnesses caused by ischemic conditions:

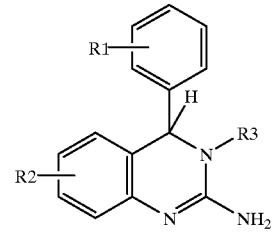

wherein: R1, R2 and R3 have the meanings indicated in the specification and claims.

13 Claims, No Drawings

USE OF 2-AMINO-3,4-DIHYDROQUINAZOLINES FOR THE PRODUCTION OF A MEDICAMENT FOR THE TREATMENT OR PROPHYLAXIS OF ILLNESSES CAUSED BY ISCHEMIC CONDITIONS

This application claims benefit under 35 U.S.C. § 119 of application no. 19951702.9, filed on Oct. 27, 1999 in Germany, which is incorporated in its entirety by reference herein.

The invention relates to the use of 2-amino-3,4-dihydroquinazolines of the formula I

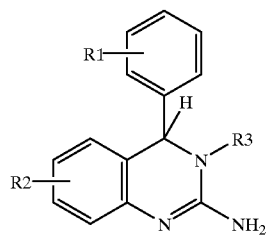

and of their pharmaceutically tolerable salts for the production of a medicament for the therapy and prophylaxis of ischemic conditions. In formula I:

R1 and R2 are hydrogen, F, Cl, Br, I, straight-chain or branched $C_1$–$C_4$-alkyl, $C_1$–$C_4$-alkoxy, R3 is hydrogen, straight-chain or branched $C_1$–$C_4$-alkyl or phenyl, the phenyl nucleus being unsubstituted or carrying one to three substituents selected from the group consisting of F, Cl, $CH_3$ and $CH_3O$.

The use of compounds of the formula I and of their salts is preferred, in which:

R1 and R2 are hydrogen, fluorine, chlorine, straight-chain or branched $C_1$–$C_4$-alkyl, $C_1C_4$-alkoxy;

R3 is hydrogen or methyl.

If one of the three substituents R1, R2 and R3 contains an asymmetric center, the invention includes compounds of S and R configuration. The compounds can be present as optical isomers, as diastereoisomers, as racemates or as mixtures thereof.

Compounds of the formula I are known from EP 530 994, where they are described as inhibitors of HIV reverse transcriptase in the indication AIDS;

U.S. Pat. No. 3,560,050, in which their analgesic, diuretic and anti-inflammatory action is described;

and from Kosasayama et al., Chem. Pharm. Bull. 27, 880 (1979) and Ishikawa et al. Ibid, 28, 1357 (1980), where it was possible to show an inhibition of platelet aggregation for 2-amino-4-phenyl-3,4-dihydroquinazoline.

Surprisingly, it has now been found that these known compounds are distinguished by inhibition of $Na^+/H^+$ exchange. Thus, as a result of their pharmacological properties, they are outstandingly suitable for the production of antiarrhythmic pharmaceuticals having a cardioprotective component for infarct prophylaxis and infarct treatment and also for the treatment of angina pectoris, where they also preventively inhibit or greatly decrease the pathophysiological processes in the formation of ischemically induced damage, in particular in the elicitation of ischemically induced cardiac arrhythmias. Because of their protective actions against pathological hypoxic and ischemic situations, the compounds of the formula I used according to the invention, as a result of inhibition of the cellular $Na^+/H^+$exchange mechanism, can serve as pharmaceuticals for the treatment of all acute or chronic damage caused by ischemia or illnesses induced primarily or secondarily thereby. This relates to their use as pharmaceuticals for surgical interventions, e.g. in organ transplantation, where the compounds used according to the invention can be used both for the protection of the organs in the donor before and during removal, for the protection of removed organs, for example during treatment with or storage thereof in physiological bath fluids, and during transfer to the recipient's body. The compounds used according to the invention are also valuable pharmaceuticals having a protective action when carrying out angioplastic surgical interventions, for example on the heart and on peripheral vessels. According to their protective action against ischemically induced damage, the compounds are also suitable as pharmaceuticals for the treatment of ischemias of the nervous system, in particular of the central nervous system, where they are suitable, for example, for the treatment of stroke or of cerebral edema. Moreover, the compounds of the formula I are also suitable for the treatment of forms of shock, such as, for example, of allergic, cardiogenic, hypovolemic and of bacterial shock.

Moreover, the compounds of the formula I used according to the invention are distinguished by strong inhibitory action on the proliferation of cells, for example fibroblast cell proliferation and the proliferation of vascular smooth muscle cells. The compounds of the formula I used according to the invention are therefore suitable as valuable therapeutics for illnesses in which cell proliferation is a primary or secondary cause, and can therefore be used as antiatherosclerotics, agents against diabetic late complications, carcinomatous diseases, fibrotic diseases such as pulmonary fibrosis, hepatic fibrosis or renal fibrosis, organ hypertrophy and hyperplasia, in particular in prostate hyperplasia and prostate hypertrophy.

The compounds used according to the invention are efficacious inhibitors of the cellular sodium/proton antiporter ($Na^+/H^+$exchanger), which is raised in numerous diseases (essential hypertension, atherosclerosis, diabetes etc.) even in those cells which are easily accessible to measurements, such as, for example, in erythrocytes, platelets or leukocytes. The compounds used according to the invention are therefore suitable as outstanding and simple scientific tools, for example in their use as diagnostics for the determination and differentiation of certain forms of hypertension, but also of atherosclerosis, of diabetes, proliferative diseases etc. Moreover, the compounds of the formula I used according to the invention are suitable for preventive therapy for the prevention of the genesis of high blood pressure, for example of essential hypertension.

It has moreover been found that compounds of the formula I used according to the invention exhibit a favorable influence on serum lipoproteins. It is generally recognized that for the formation of arteriosclerotic vascular changes, in particular of coronary h eart disease, excessively high blood fat values, so-called hyperlipoproteinemias, are an essential risk factor. The lowering of raised serum lipoproteins therefore has exceptional importance for the p rophyl axis and the regression of atherosclerotic changes. In addition to the reduction of the total serum cholesterol, the lowering of the proportion of specific atherogenic lipid fractions of this total cholesterol, in particular of the low density lipoproteins (LDL) and of the very low density lipoproteins (VLDL) has particular importance, as these lipid fractions are an atherogenic risk factor. However, a protective function against coronary heart disease is ascribed to the high density lipoproteins. Accordingly, hypolipidemics should be able to lower not only the total cholesterol, but in particular the VLDL and LDL serum cholesterol fractions. It has now been found that the compounds of the formula I used according to the invention exhibit valuable therapeutically utilizable properties with respect to the influencing of the serum lipid levels. Thus they significantly reduce the raised serum concentration of LDL and VLDL, such as are to be observed, for example, due to increased dietetic intake of a cholesterol- and lipid-rich diet or in pathological metabolic changes, for example genetically related hyperlipidemias. They can therefore be used for the prophylaxis and for the regression of atherosclerotic changes, in that they exclude a causal risk factor. These include not only the primary hyperlipidemias, but also certain secondary hyperlipidemias, such as occur, for example, in diabetes. Moreover, the compounds of the formula I used according to the invention lead to a marked reduction in the infarcts induced by metabolic anomalies and in particular to a significant decrease in the induced infarct size and its degree of severity. Furthermore, the compounds of the formula I used according to the invention lead to an effective protection against endothelial damage induced by metabolic anomalies. With this protection of the vessels against the syndrome of endothelial dysfunction, compounds of the formula I are useful pharmaceuticals for the prevention and treatment of coronary vasospasms, of atherogenesis and of atherosclerosis, left-ventricular hypertrophy and dilated cardiomyopathy, and thrombotic diseases.

The compounds I used according to the invention are therefore advantageously used for the production of a medicament for the treatment of hypercholesterolemia;

for the production of a medicament for the prevention of atherogenesis;

for the production of a medicament for the prevention and treatment of atherosclerosis;

for the production of a medicament for the prevention and treatment of diseases which are caused by raised cholesterol levels;

for the production of a medicament for the prevention and treatment of illnesses which are caused by endothelial dysfunction;

for the production of a medicament for the prevention and treatment of atherosclerosis-induced hypertension;

for the production of a medicament for the prevention and treatment of atherosclerosis-induced thromboses;

for the production of a medicament for the prevention and treatment of hypercholesterolemia- and endothelial dysfunction-induced ischemic damage and postischemic reperfusion damage;

for the production of a medicament for the prevention and treatment of hypercholesterolemia- and endothelial dysfunction-induced cardiac hypertrophies and cardiomyopathies;

for the production of a medicament for the prevention and treatment of hypercholesterolemia- and endothelial dysfunction-induced coronary vasospasms and myocardial infarcts;

for the production of a medicament for the treatment of the illnesses mentioned in combinations with hypotensive substances, preferably with angiotensin converting enzyme (ACE) inhibitors and angiotensin receptor antagonists. A combination of an NHE inhibitor of the formula I with an active compound lowering the blood fat level, preferably with an HMG-CoA reductase inhibitor (e.g. lovastatin or pravastatin), the latter producing a hypolipidemic action and thereby increasing the hypolipidemic properties of the NHE inhibitor of the formula I, proves to be a favorable combination having increased action and decreased use of active compound.

The use of the sodium/proton exchange inhibitors of the formula I for the production of novel pharmaceuticals for lowering increased blood fat levels, and the combination of sodium/proton exchange inhibitors with pharmaceuticals having hypotensive and/or hypolipidemic action, are claimed.

Pharmaceuticals which contain a compound I can in this case be administered orally, parenterally, intravenously, rectally or by inhalation, the preferred administration being dependent on the particular course of the disease. The compounds I can be used in this case on their own or together with pharmaceutical excipients, namely both in veterinary and in human medicine.

The person skilled in the art is familiar on the basis of his/her expert knowledge with excipients which are suitable for the desired pharmaceutical formulation. In addition to solvents, gel-forming agents, suppository bases, tablet excipients, and other active compound carriers, it is possible to use, for example, antioxidants, dispersants, emulsifiers, antifoams, flavor corrigents, preservatives, solubilizers or colorants.

For an oral administration form, the active compounds I used according to the invention are mixed with the additives suitable for this, such as vehicles, stabilizers, or inert diluents, and are brought by the customary methods into the suitable administration forms, such as tablets, coated tablets, hard gelatin capsules, aqueous, alcoholic or oily solutions. Inert carriers which can be used are, for example, gum arabic, magnesia, magnesium carbonate, potassium phosphate, lactose, glucose or starch, in particular corn starch. In this case, preparation can be carried out either as dry or moist granules. Possible oily vehicles or solvents are, for example, vegetable or animal oils, such as sunflower oil or cod-liver oil.

For subcutaneous or intravenous administration, the active compounds used according to the invention, if desired with the substances customary therefor such as solubilizers, emulsifiers or further excipients, are brought into solution, suspension or emulsion. Suitable solvents are, for example, water, physiological saline solution or alcohols, e.g. ethanol, propanol, glycerol, in addition also sugar solutions such as glucose or mannitol solutions, or alternatively a mixture of the various solvents mentioned.

Suitable pharmaceutical formulations for administration in the form of aerosols or sprays are, for example, solutions, suspensions or emulsions of the active compound of the formula I in a pharmaceutically acceptable solvent, such as, in particular, ethanol or water, or a mixture of such solvents. If required, the formulation can also contain further pharmaceutical excipients such as surfactants, emulsifiers and stabilizers and also a propellant. Such a preparation customarily contains the active compound in a concentration of approximately 0.1 to 10, in particular of approximately 0.3 to 3% by weight.

The dose of the active compound of the formula I to be administered and the frequency of administration depend on the potency and duration of action of the compounds used; moreover also on the nature and severity of the illness to be treated and on the sex, age, weight and individual responsiveness of the mammal to be treated.

On average, the daily dose of a compound of the formula I in the case of a patient weighing approximately 75 kg is at least 0.001 mg/kg, preferably 0.01 mg/kg, to at most 10 mg/kg, preferably 1 mg/kg, of body weight. In the case of acute episodes of the illness, for example immediately after suffering a cardiac infarct, even higher and especially more frequent doses may also be necessary, e.g. up to 4 individual doses per day. In particular in the case of i.v. administration, for example in the case of an infarct patient in the intensive care unit, up to 200 mg per day may be necessary.

EXPERIMENTAL SECTION

List of Abbreviations

| | |
|---|---|
| DMSO | Dimethyl sulfoxide |
| RT | Room temperature |
| EA | Ethyl acetate (EtOAc) |
| m.p. | melting point |
| eq. | equivalent |

Example 1

2-Amino-4-(4-methoxyphenyl)-3,4-dihydroquinazoline Hydrochloride

Colorless solid, m.p. 169° C., $M^++H=254$.
Synthesis Route:
2-Aminophenyl 4-methoxyphenyl ketone is reacted with 1.2 eq of formamidine hydrochloride in the presence of potassium carbonate with heating in DMSO to give the corresponding quinazoline. After aqueous work-up, the crude product is hydrogenated using 10% Pd/C in ethanol, and subsequent column chromatography and hydrochloride formation using ethereal hydrogen chloride affords the product as a solid.

Example 2

2-Amino-4-(3,4-dimethoxyphenyl)-3,4-dihydroquinazolinium Fumarate

Colorless solid, m.p. 179° C., $M^++H=284$.
The synthesis is carried out analogously to Example 1 using 2-amino-phenyl3,4-dimethoxyphenyl ketone. For salt formation, the base is reacted with 1 eq of fumaric acid in EA.

Example 3

2-Amino4-(3,4-dimethoxyphenyl)-3-methyl-3,4-dihydro-quinazolinium Fumarate

Colorless solid, m.p. 202° C., $M^++H=298$.
Synthesis Route:
Starting from 2-aminophenyl-3,4-dimethoxyphenyl ketone, the corresponding benzhydrylamine is prepared using methylamine/titanium tetrachloride and subsequent reduction using sodium borohydride. The crude product is cyclized to the 3,4-dihydroquinazoline using an excess of cyanogen bromide and subjected to column chromatography. Subsequent salt formation is carried out as described in Example 2).

PHARMACOLOGICAL DATA

Inhibition of the $Na^+/H^+$ Exchanger of Rabbit Erythrocytes

White New Zealand rabbits (Ivanovas) received a standard diet with 2% cholesterol for six weeks in order to activate the $Na^+/H^+$ exchange and thus to be able to determine the $Na^+$ influx into the erythrocytes via $Na^+/H^+$ exchange by flame photometry. The blood was removed from the auricular arteries and rendered uncoagulable by means of 25 IU of potassium heparin. A part of each sample was used for the duplicate determination of the hematocrit by centrifugation. Aliquots of 100 μl in each case served for the measurement of the $Na^+$ starting content of the erythrocytes.

In order to determine the amiloride-sensitive sodium influx, 100 μl of each blood sample in 5 ml in each case of a hyperosmolar salt/sucrose medium (mmol/I: 140 NaCl, 3 KCl, 150 sucrose, 0.1 ouabain, 20 tris-hydroxymethyl-aminomethane) were incubated at pH 7.4 and 37° C. The erythrocytes were then washed three times with ice-cold $MgCl_2$/ouabain solution (mmol/I: 112 $MgCl_2$, 0.1 ouabain) and hemolyzed in 2.0 ml of distilled water. The intracellular sodium content was determined by flame photometry.

The $Na^+$ net influx was calculated from the difference between sodium starting values and the sodium content of the erythrocytes after incubation. The amiloride-inhibitable sodium influx followed from the difference in the sodium content of the erythrocytes after incubation with and without amiloride $3\times10^{-4}$ mol/I. The procedure was the same in the case of the compounds according to the invention.

RESULTS

Inhibition of the $Na^+/H^+$ Exchanger

Example $IC_{50}$ (mol/I)
1: $3.4\times10^{-6}$
2: $3.2\times10^{-6}$
3: $4.1\times10^{-6}$

We claim:
1. A method of treating or preventing of an ischemic condition, comprising administering to a host in need thereof an effective amount of a compound of the formula I

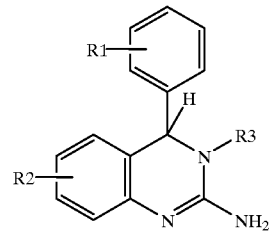

or of a pharmaceutically tolerable salt thereof, in which:
R1 and R2 are hydrogen, F, Cl, Br, I, straight-chain or branched $C_1$–$C_4$-alkyl or $C_1$–$C_4$-alkoxy, and
R3 is hydrogen, straight-chain or branched $C_1$–$C_4$-alkyl or phenyl,
the phenyl nucleus being unsubstituted or carrying one to three substituents selected from the group consisting of F, Cl, $CH_3$ and $CH_3O$.

2. A method of claim 1, wherein in formula I:
R1 and R2 are hydrogen, fluorine, chlorine, straight-chain or branched $C_1$–$C_4$-alkyl or $C_1$–$C_4$-alkoxy;
R3 is hydrogen or methyl.

3. A method of claim 1, which comprises treating or preventing cardiac infarct.

4. A method of claim 1, which comprises treating or preventing angina pectoris.

5. A method of claim 1, wherein the ischemic condition is of the heart.

6. A method of claim 1, wherein the ischemic condition is of the peripheral or central nervous system.

7. A method of claim 1, which comprises treating or preventing stroke.

8. A method of claim 1, wherein the ischemic condition is of peripheral organs and limbs.

9. A method of claim 1, which comprises treating of a state of shock.

10. A method of preserving or protecting an organ transplant for surgical measures, comprising bringing into contact with the organ transplant an effective amount of a compound of the formula I

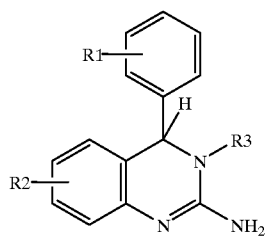

or of a pharmaceutically tolerable salt thereof, in which:
R1 and R2 are hydrogen, F, Cl, Br, I, straight-chain or branched $C_1$–$C_4$-alkyl or $C_1$–$C_4$-alkoxy, and
R3 is hydrogen, straight-chain or branched $C_1$–$C_4$-alkyl or phenyl,
the phenyl nucleus being unsubstituted or carrying one to three substituents selected from the group consisting of F, Cl, $CH_3$ and $CH_3O$.

11. A method of protecting a transplant organ during surgical operations and organ transplantations, comprising administering to a host in need of such protection an effective amount of formula I:

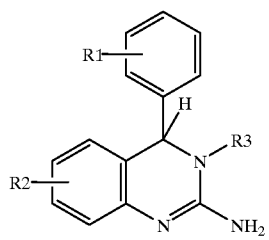

or of a pharmaceutically tolerable salt thereof, in which:
R1 and R2 are hydrogen, F, Cl, Br, I, straight-chain or branched $C_{1\text{-}C_4}$-alkyl or $C_1$–$C_4$-alkoxy, and
R3 is hydrogen, straight-chain or branched $C_1$–$C_4$-alkyl or phenyl,
the phenyl nucleus being unsubstituted or carrying one to three substituents selected from the group consisting of F, Cl, $CH_3$ and $CH_3O$.

12. A method for treating an illness where cell proliferation is a primary or secondary cause, comprising administering to a host in need of such treatment an effective amount of a compound of formula I

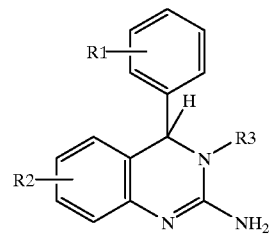

or of a pharmaceutically tolerable salt thereof, in which:
R1 and R2 are hydrogen, F, Cl, Br, I, straight-chain or branched $C_1$–$C_4$-alkyl or $C_1$–$C_4$-alkoxy, and
R3 is hydrogen, straight-chain or branched $C_{1\text{-}C_4}$-alkyl or phenyl,
the phenyl nucleus being unsubstituted or carrying one to three substituents selected from the group consisting of F, Cl, $CH_3$ and $CH_3O$.

13. A method of treating or preventing a disorder of fat metabolism, comprising administering to a host in need of the treatment or prevention an effective amount of a compound of formula I:

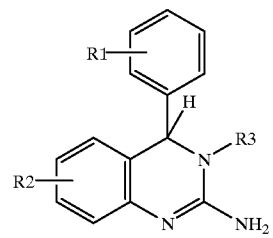

or of a pharmaceutically tolerable salt thereof, in which:
R1 and R2 are hydrogen, F, Cl, Br, I, straight-chain or branched $C_1$–$C_4$-alkyl or $C_1$–$C_4$-alkoxy, and
R3 is hydrogen, straight-chain or branched $C_1$–$C_4$-alkyl or phenyl,
the phenyl nucleus being unsubstituted or carrying one to three substituents selected from the group consisting of F, Cl, $CH_3$ and $CH_3O$.

* * * * *